(12) United States Patent
Percy et al.

(10) Patent No.: US 9,845,498 B2
(45) Date of Patent: Dec. 19, 2017

(54) LUMINESCENCE DETECTION METHOD

(71) Applicant: 3M INNOVATIVE PROPERTIES COMPANY, St. Paul, MN (US)

(72) Inventors: Neil Percy, St. Paul, MN (US); Gregory W. Sitton, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 129 days.

(21) Appl. No.: 14/487,144

(22) Filed: Sep. 16, 2014

(65) Prior Publication Data

US 2015/0004681 A1 Jan. 1, 2015

Related U.S. Application Data

(62) Division of application No. 14/111,573, filed as application No. PCT/US2012/034155 on Apr. 19, 2012, now Pat. No. 8,852,894.

(60) Provisional application No. 61/478,251, filed on Apr. 22, 2011.

(51) Int. Cl.
| | | |
|---|---|---|
| *C12Q 1/68* | (2006.01) | |
| *C12P 19/34* | (2006.01) | |
| *G01N 21/03* | (2006.01) | |
| *G01N 21/76* | (2006.01) | |

(52) U.S. Cl.
CPC .............. *C12Q 1/686* (2013.01); *G01N 21/03* (2013.01); *G01N 21/76* (2013.01); *G01N 21/763* (2013.01)

(58) Field of Classification Search
CPC ..................................................... C12Q 1/686
USPC ...................... 435/4, 6.1, 6.12, 91.2; 422/430
See application file for complete search history.

(56) References Cited

U.S. PATENT DOCUMENTS

| | | |
|---|---|---|
| 4,755,356 A | 7/1988 | Robbins et al. |
| 5,968,548 A | 10/1999 | Wong et al. |
| 6,524,530 B1 | 2/2003 | Igarashi et al. |
| 7,097,981 B1 | 8/2006 | Gicquel et al. |
| 7,109,315 B2 | 9/2006 | Bryan et al. |
| 2001/0039058 A1 | 11/2001 | Iheme et al. |

(Continued)

FOREIGN PATENT DOCUMENTS

| | | |
|---|---|---|
| EP | 0 569 835 | 11/1993 |
| JP | 57-70459 | 4/1982 |

(Continued)

OTHER PUBLICATIONS

"Biological Test Methods for Assessing Contaminated Land—Stage 2—A demonstration of the use of a framework for the ecological risk assessment of land contamination" from Environment Agency; Aug. 2004; ISBN: 1844322963; 116 pgs.

(Continued)

*Primary Examiner* — Jezia Riley

(57) ABSTRACT

A method of detecting an analyte is provided. The method includes providing a sample, a container 110 with a wall 115, and a catalyst for a luminescent reaction. The wall includes a colored portion 115b. The method further comprises forming a reaction in the container and detecting the presence or absence of light emitted from the reaction mixture in the container. Detecting light emitted from the container can comprise detecting light passing through the colored portion. The colored portion can be detected visually and the color can be associated with the identity of an analyte-specific reagent disposed in the container. Kits comprising the container and a catalyst for a luminescent reaction are also provided.

11 Claims, 2 Drawing Sheets

(56) References Cited

U.S. PATENT DOCUMENTS

| | | |
|---|---|---|
| 2004/0200738 A1 | 10/2004 | Rovelli et al. |
| 2006/0088857 A1 | 4/2006 | Attiya et al. |
| 2008/0251490 A1 | 10/2008 | Livingston et al. |
| 2010/0216147 A1 | 8/2010 | Upton et al. |

FOREIGN PATENT DOCUMENTS

| | | |
|---|---|---|
| JP | 04-503566 | 6/1992 |
| JP | 11-45601 | 2/1999 |
| JP | 2004-524856 | 8/2004 |
| JP | 2009-510475 | 3/2009 |
| JP | 2011-58868 | 3/2011 |
| JP | 2012-516429 | 7/2012 |
| WO | WO 90/05903 | 5/1990 |
| WO | WO 96/41878 | 12/1996 |
| WO | WO 00-70011 | 11/2000 |
| WO | WO 02/090586 | 11/2002 |
| WO | WO 02/099121 | 12/2002 |
| WO | WO 2006-078289 | 7/2006 |
| WO | WO 2006/108079 | 10/2006 |
| WO | WO 2007/041507 | 4/2007 |
| WO | WO 2010/085844 | 8/2010 |
| WO | WO 2010/132453 | 11/2010 |

OTHER PUBLICATIONS

Gandelman, O.A. et al.; "Novel Bioluminescent Quantitative Detection of Nucleic Acid Amplification in Real-Time"; Plos One; vol. 5, No. 11; 2010; pp. e14155- (13 pgs).

Sambrook, J. et al.; Molecular Cloning—A Laboratory Manual, Third Edition, vol. 2, Cold Spring Harbor Laboratory Press, Cold Spring Harbor, NY, 2001, Title, copyright and Table of Contents 18 pages.

Wacker, Ron; presentation entitled "Immuno-PCR-Maximizing Immunoassay Sensitivity" from Infectious Diseases Workshop I; Chimera Biotec; 2006; 33 pgs.

Brochure entitled "Cybersense Technical Note CTN200505—The Use of ROTAS™ for screening soils and waters for risk to human health" from Cybersense Biosystems Limited; 2005; 1 pg.

Brochure entitled "ROTAS (Rapid On-site Toxicity Audit System) Biological Assay—Cybersense Technical Product Note CTPN200531" from Cybersense Biosystems Limited; 2005; 2 pgs.

Brochure entitled "Cybersense Technical Note CTN200506—A review of the use of ROTAS™ in the ecotoxicological testing of soil" from Cybersense Biosystems Limited; 2006; 2 pgs.

Brochure entitled "Lumora PDQ" from Panchromos; retrieved from the internet on Jul. 31, 2013 from www.panchromos.com; 3 pgs.

Brochure entitled "An ultra-sensitive, versatile, and affordable single tube luminometer fro Life Science research. 20/20ⁿ Single Tube Luminometer" from Turner BioSystems; 2008; 4 pgs.

LUMINESCENCE DETECTION METHOD

CROSS REFERENCE TO RELATED APPLICATIONS

This application is a divisional of U.S. Ser. No. 14/111,573, filed Oct. 14, 2013 (now allowed), which is a national stage filing under 35 U.S.C. 371 of PCT/US2012/034155, filed Apr. 19, 2012, which claims priority to U.S. Provisional Patent Application No. 61/478,251, filed Apr. 22, 2011, which is incorporated herein by reference in its entirety.

BACKGROUND

Laboratories often perform a variety of test procedures such as, for example, tests to determine the presence or identity of an etiological agent. Each test may include an analyte-specific reagent (e.g., an enzyme substrate, a nucleic acid primer or probe, an antibody, a monoclonal antibody, or a receptor) that can detect the presence of a particular microorganism in a sample.

Laboratory tests for etiological agents are frequently performed in individual containers (e.g., tubes or microtubes). Additionally, it is not uncommon to process a batch of tests at the same time to improve the efficiency of the laboratory operations. Because similar tests are often performed in identical-appearing tubes, the laboratory technicians use labels to distinguish tubes containing different sample materials and/or analyte-specific reagents.

Labels are routinely applied to reaction tubes to identify the contents of the tubes. The labels may be written on the tube or a corresponding cap. Permanent, waterproof ink is used to prevent the label from washing or rubbing off during handling. Alternatively, an adhesive label, bearing a description of the contents of the tube, is attached to the tube.

The labels often include a large amount of information related to the contents of the tube (e.g., sample identity, date, the type of test or reagent-specific analyte, the operator). Bar-code labels are used in some instances, so that a relatively large amount of information can be incorporated into a relatively small label.

SUMMARY

In general, the invention relates to a method of detecting an analyte. In particular, the method is directed to the detection of the presence of an analyte by detecting a light-emitting reaction. The method further relates to a colored container that can be used in the method. Surprisingly, a variety of colored containers, which are visually distinguishable from each other, can be used in a detection method that requires the detection of light that passes through the colored walls of the container. Advantageously, the colored containers provide instantaneous visual identification of at least one component of the reaction, thereby reducing the possibility of laboratory error.

In one aspect, the present disclosure provides a method of detecting an analyte. The method can comprise providing a sample, a catalyst for a luminescent reaction, and a container; forming a reaction mixture in the container; and detecting light emitted from the reaction mixture in the container. The reaction mixture can comprise the sample and the catalyst. The container can include at least one wall. At least a portion of the wall comprises a coloring agent.

In any of the above embodiments, the container can be adapted for use in a luminometer. In any of the above embodiments, forming a reaction mixture further can comprise forming a reaction mixture to facilitate a luminescent reaction. In any of the above embodiments, the portion can be visibly-colored. In any of the above embodiments, detecting light from the luminescent reaction further can comprise operably positioning the container in a luminometer comprising a detector. In any of the above embodiments, operably positioning the container further can comprise positioning the container such that at least a part of the portion is positioned between the reaction mixture and the detector. In any of the above embodiments, detecting light further can comprise quantifying an amount of light.

In any of the above embodiments, providing the catalyst further can comprise providing a dry, rehydratable catalyst. In any of the above embodiments, providing a catalyst can comprise providing luciferase. In any of the above embodiments, wherein providing the detection reagent and the container further can comprise providing the container with the catalyst disposed therein.

In any of the above embodiments, the method further can comprise providing an analyte-specific reagent. In any of the above embodiments, providing an analyte-specific detection reagent further can comprise providing a polynucleotide. In any of the above embodiments, forming a reaction mixture further can comprise forming a reaction mixture to facilitate nucleic acid amplification. In any of the above embodiments, the color of the portion can be associated with the identity of the analyte-specific reagent disposed in the container. In any of the above embodiments, the analyte can comprise DNA or RNA.

In any of the above embodiments, the coloring agent can comprise a red coloring agent, a blue coloring agent, a yellow coloring agent, a green coloring agent, a mixture of any two or more of the foregoing coloring agents or a combination of any two or more of the foregoing coloring agents.

In another aspect, the present disclosure provides a kit. The kit can comprise a detection reagent and a container. The container can comprise at least one wall. At least a portion of the wall can comprise a coloring agent. The container can be adapted for use in a luminometer.

In any embodiment of the kit, the portion can be visibly-colored. In any embodiment of the kit, the detection reagent can be an analyte-specific reagent. In any embodiment of the kit, the color of the portion can be associated with the identity of the analyte-specific reagent. In any embodiment, the kit further can comprise a cell lysis agent, RNA polymerase, or DNA polymerase. In any embodiment of the kit, the color can comprise red, yellow, blue, green, mixtures thereof, or combinations thereof.

The terms "analyte", as used herein, refers to various molecules (e.g., a nucleotide, a nucleic acid a protein, an enzyme) or epitopes of molecules (e.g., different binding sites of a protein, a glycoprotein or a polysaccharide), or whole cells of a microorganism. The analyte may be characteristic of a microorganism (i.e., bacterium, yeast, mold, or virus) or a group of microorganisms of interest and, thus, the presence of the analyte in a sample is indicative of the presence of the microorganism in the sample.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a container can be interpreted to mean "one or more" containers.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Figure 1:
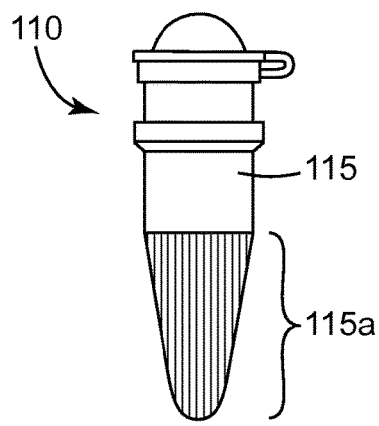
FIG. 1 is a side view of one embodiment of a container with a portion comprising a coloring agent, according to the present disclosure.

A trend in laboratory testing is the use of microvolume tests. This trend is being driven by the expense of particular reagents (e.g., enzymes, enzyme reagents, dyes, monoclonal antibodies) and the development of sample preparation technology that can concentrate analyte molecules into very small volumes, thereby enhancing the kinetics of detection reactions. Furthermore, there is a trend toward using a particular instrument (e.g., a real-time PCR thermocycler) to perform a large number of tests, many of which include analyte-specific reagents (i.e. primers and/or probes). Such instruments often use standardized containers (e.g., microtubes) in which all of the tests are conducted. Because the standardized containers appear identical, laboratory technicians depend on the use of labels to distinguish the contents of each container.

The labels can be used to record a variety of important information related to the contents of each container (e.g., sample identification, sample source, date, operator, type of test, analyte-specific reagents, lot numbers, and the like). Because the containers are so small, it can be difficult to record all of the information on a label that will fit on the available surface area of the container and/or its cap. The use of bar-codes can associate a particular sample with a unique code/number, thereby permitting the technician to record large amounts of information associated with the bar-code. However, such codes may only be deciphered easily by a bar-code reader connected to a database in which the information is stored, making it difficult for a technician instantly to visually recognize important attributes of the contents of any given container.

Another drawback associated with the use of labels is that they can obscure a portion or all of the walls or cap of a container in which the test is conducted. This can be a problem for tests that require optical detection of a reaction occurring in the container (e.g., a reaction in which the emission of light by luminescence is the basis for detecting the presence or absence of an analyte). The label may substantially absorb light from a luminescent reaction, as the light is passing out of the container on a path toward an optical detector (e.g. a photomultiplier a photodiode, a charge-coupled device (CCD), a complementary metal-oxide-semiconductor (CMOS), a semiconductor, photographic film) and/or as the light is passing toward a reflective surface intended to direct the light toward the optical detector, thereby reducing the potential sensitivity of the detection system.

Thus, there are at least two problems encountered by a technician who attempts to perform a luminescence-based assay in a microcontainer: i) marking a particular microcontainer such that one or more critical component contained in the microcontainer is easily and instantly recognizable by a technician or an instrument and ii) avoiding substantial interference by the mark with the optical detection of a reaction in the microcontainer. The inventive method provides a means to mark a container in a way that, even though the means absorbs light and lies directly in the path between a luminescent reaction and a photodetector, surprisingly, it does not substantially interfere with the detection of the luminescent reaction. Without being bound by theory, it is believed that a human observer easily detects the color of the tube because the observer typically is visually detecting light (from a source external to the microcontainer) that passes through at least two layers (e.g., walls) of the colored material. Thus, apparent absorbance of the external light is at least doubled when detected by the human eye. In contrast, light emitted by a luminescent reaction within the microcontainer only passes through one wall as it is traveling on a path to the detector. Advantageously, this permits easy visible detection of the tube color with relatively little interference (i.e., absorbance) of the light emitted from a reaction in the microcontainer.

The method comprises providing a sample, a detection reagent, and a container. The container includes at least one wall that forms an opening and an interior reservoir. The sample can be suspected of comprising an analyte (e.g., an analyte associated with a particular microorganism or group of microorganisms). Microorganisms of particular interest include prokaryotic and eukaryotic organisms, particularly Gram positive bacteria, Gram negative bacteria, fungi, protozoa, *mycoplasma*, yeast, viruses, and even lipid-enveloped viruses. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp. as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis, Streptococcus pneumoniae, S. agalactiae, S. pyogenes, Enterococcus faecalis,* Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis, Pseudomonas aeruginosa, Escherichia coli, Aspergillus niger, A. fumigatus, A. clavatus, Fusarium solani, F. oxysporum, F. chlamydosporum, Listeria monocytogenes, Listeria ivanovii, Vibrio cholera, V. parahaemolyticus, Salmonella cholerasuis, S. typhi, S. typhimurium, Candida albicans, C. glabrata, C. krusei, Enterobacter sakazakii, E. coli* O157 and multiple drug resistant Gram negative rods (MDR).

Gram positive and Gram negative bacteria are of particular interest. Of even more interest are Gram positive bacteria, such as *Staphylococcus aureus.* Typically, these can be detected by detecting the presence of a cell-wall component characteristic of the bacteria, such as a cell-wall protein. Also, of particular interest are antibiotic resistant microbes including MRSA, VRSA, VISA, VRE, and MDR. Typically, these can be detected by additionally detecting the presence of an internal cell component, such as a membrane protein, transport protein, enzyme, etc., responsible for antibiotic resistance.

In some embodiments, the analyte may be a biomolecule that is a reactant for a luminescent reaction (e.g., ATP, luciferase). In some embodiments, the analyte may be a biomolecule (e.g., a nucleic acid) that participates in a reaction or in a series of reactions that generate a reactant for a luminescent reaction. A nonlimiting example of a series of reactions that generate a reactant for a luminescent reaction in response to the presence of a specific nucleic acid analyte is the LAMP-BART assay described by Gandelman et al. ("Novel Bioluminescent Quantitative Detection of Nucleic Acid Amplification in Real-Time", 2010, Plos ONE, volume 5 (11), article e14155, published at www.plosone.org in November 2010).

Figure 2A:
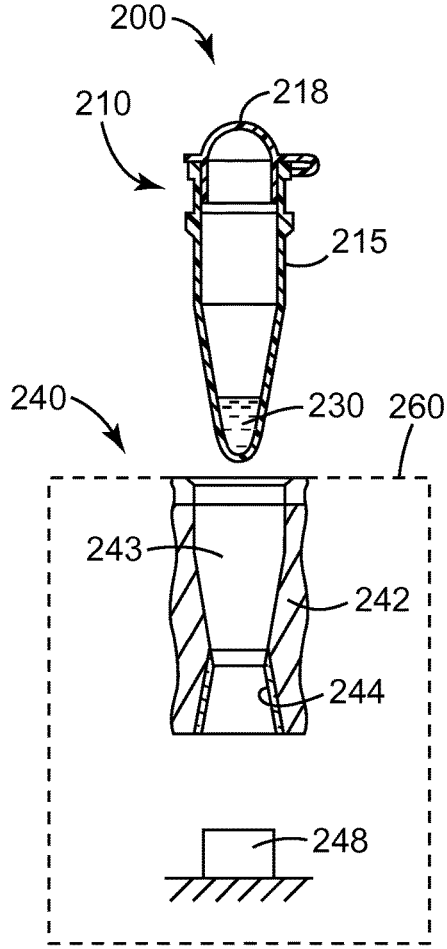
FIG. 2A is an exploded cross-sectional schematic view of one embodiment of a container with a portion comprising a coloring agent and a luminescence reader, according to the present disclosure.
Figure 2B:
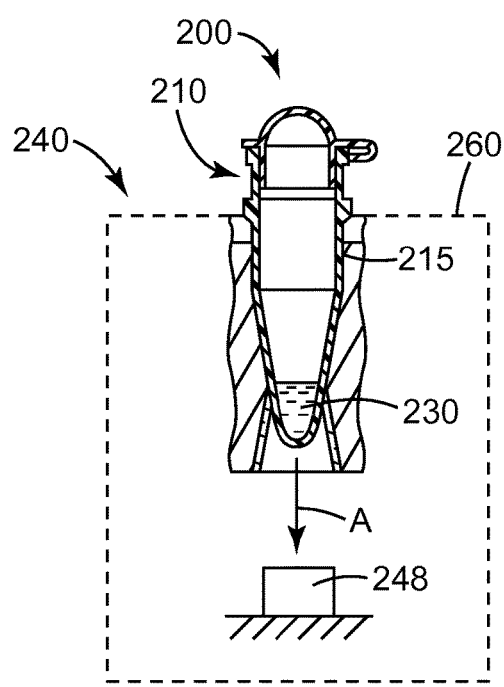
FIG. 2B is a cross-sectional schematic view of the container of FIG. 2A operationally coupled with the luminescence reader of FIG. 2A.

FIG. 1 shows one embodiment of a container 110 according to the present disclosure. The container 110 comprises a unitary wall 115 that forms an opening 120 and an interior reservoir 130. Optionally, a cap (not shown) may be used to seal the opening 120. The container 110 is adapted for use in a luminometer. "Adapted for use in a luminometer", as used herein, means the container 110 has a shape and dimensions that permit it to be received in a luminometer so that light emitted from the container, or contents (e.g., a reaction mixture) therein, can be detected and, optionally, measured by the luminometer. In any embodiment, the container 110 is configured (i.e., has a suitable size and shape) to be received in a thermal transfer device that is operably coupled to a light-detecting detector, as shown in FIGS. 2A-B, for example. Accordingly, in these embodiments, light emitted from the container 110, or contents therein, can be received by the light-detecting detector while, simultaneously, the temperature of the container and contents therein is optionally controlled and/or modulated by the thermal transfer device.

The container 110 can be fabricated from a material (e.g., glass; polymeric materials such as polyethylene, polypropylene, for example) having an optical clarity and optical transmissivity that does not substantially prevent light (e.g. visible wavelengths of light from a luminescent reaction) from passing through the wall 115 to a light-detecting detector. In some embodiments, the container can be a test tube, a reaction tube, or a microcentrifuge tube. The 20/20" Single Tube Luminometer, available from Turner Biosystems (Sunnyvale, Calif.), includes a sample adapter that permits the use of 1.5 mL microcentrifuge tubes in the luminometer, for example.

The wall 115 of the container 110 further comprises a portion 115*b* that includes a coloring agent. In some embodiments (not shown), the portion that includes a coloring agent may be the cap, wherein the light detected from a luminescent reaction in the tube is detected after the light has passed through the cap. In some embodiments, the coloring agent can be detected using an instrument (e.g., using a spectrophotometer). In preferred embodiments, color associated with the portion 115*b* of the wall 115 comprising the coloring agent can be detected visually. The portion can include any detectable fraction of the surface area of the wall 115. In some embodiments, the portion comprises up to about 1 percent of the surface area of the wall. In some embodiments, the portion comprises up to about 2 percent of the surface area of the wall. In some embodiments, the portion comprises up to about 5 percent of the surface area of the wall. In some embodiments, the portion comprises up to about 10 percent of the surface area of the wall. In some embodiments, the portion comprises up to about 15 percent of the surface area of the wall. In some embodiments, the portion comprises up to about 20 percent of the surface area of the wall. In some embodiments, the portion comprises up to about 30 percent of the surface area of the wall. In some embodiments, the portion comprises up to about 40 percent of the surface area of the wall. In some embodiments, the portion comprises up to about 50 percent of the surface area of the wall. In some embodiments, the portion comprises up to about 60 percent of the surface area of the wall. In some embodiments, the portion comprises up to about 70 percent of the surface area of the wall. In some embodiments, the portion comprises up to about 80 percent of the surface area of the wall. In some embodiments, the portion comprises up to about 90 percent of the surface area of the wall. In some embodiments, the portion comprises up to about 95 percent of the surface area of the wall. In some embodiments, the portion comprises up to about 99 percent of the surface area of the wall. In some embodiments, the portion comprises up to the entire surface area of the wall. In some embodiments, the portion comprises at least about 1 percent of the surface area of the wall. In some embodiments, the portion comprises at least about 2 percent of the surface area of the wall. In some embodiments, the portion comprises at least about 5 percent of the surface area of the wall. In some embodiments, the portion comprises at least about 10 percent of the surface area of the wall. In some embodiments, the portion comprises at least about 15 percent of the surface area of the wall. In some embodiments, the portion comprises at least about 20 percent of the surface area of the wall. In some embodiments, the portion comprises at least about 30 percent of the surface area of the wall. In some embodiments, the portion comprises at least about 40 percent of the surface area of the wall. In some embodiments, the portion comprises at least about 50 percent of the surface area of the wall. In some embodiments, the portion comprises at least about 60 percent of the surface area of the wall. In some embodiments, the portion comprises at least about 70 percent of the surface area of the wall. In some embodiments, the portion comprises at least about 80 percent of the surface area of the wall. In some embodiments, the portion comprises at least about 90 percent of the surface area of the wall. In some embodiments, the portion comprises at least about 95 percent of the surface area of the wall. In some embodiments, the portion comprises at least about 99 percent of the surface area of the wall.

In some embodiments, the coloring agent is a pigment and/or a dye incorporated into the material (e.g. glass, polymer resin) from which the container 110 is formed. Alternatively or additionally, in some embodiments (not shown) the container 110 further comprises a layer (e.g., a coating or a film layer) coupled to a surface (e.g., the inner surface or the outer surface) portion 115b of the wall 115. The layer can comprise a coloring agent. The coloring agent can comprise a red coloring agent, a blue coloring agent, a yellow coloring agent, a green coloring agent, a mixture of any two or more of the foregoing coloring agents or a combination of any two or more of the foregoing coloring agents.

As with the container 110, the portion 115b of the wall 115 comprising the coloring agent has an optical clarity and optical transmissivity that does substantially prevent the light (e.g. visible wavelengths of light from a luminescent reaction) from passing through the portion 115b to a light-detecting detector. In a preferred embodiment, relative to a similar container that does not comprise a coloring agent, the container comprising a portion 115b having a coloring agent permits the transmission of at least about 50% or more of the light emitted from a luminescent reaction. In a more preferred embodiment, relative to a similar container that does not comprise a coloring agent, the container comprising a portion 115b having a coloring agent permits the transmission of at least about 75% or more of the light emitted from a luminescent reaction. In a more preferred embodiment, relative to a similar container that does not comprise a coloring agent; the container comprising a portion 115b having a coloring agent permits the transmission of at least about 85% or more of the light emitted from a luminescent reaction. In a more preferred embodiment, relative to a similar container that does not comprise a coloring agent; the container comprising a portion 115b having a coloring agent permits the transmission of at least about 90% or more of the light emitted from a luminescent reaction. In a more preferred embodiment, relative to a similar container that does not comprise a coloring agent; the container comprising a portion 115b having a coloring agent permits the transmission of at least about 95% or more of the light emitted from a luminescent reaction.

The opening 120 of the container 110 permits the transfer of materials (not shown) into the reservoir 130 of the container 110. The materials can include liquid and/or solid materials to facilitate a luminescent reaction. Nonlimiting examples of suitable materials to facilitate a luminescent reaction include a liquid medium (e.g., water, a buffer solution), an enzyme (e.g., luciferase, alkaline-phosphatase), an enzyme substrate (e.g., luciferin; ATP; 2-chloro-5-(4-methoxyspiro[1,2-dioxetane-3,2'-(5-chlorotricyclo [3.3.1.1$^{3,7}$]decan])-4-yl]-1-phenyl phosphate (CDP-STAR Chemiluminescent alkaline phosphatase reagent available from Sigma-Aldrich, St. Louis, Mo.)), a chemiluminescent reagent (e.g., luminol), and a cell lysis reagent (e.g., a detergent, TRITON X-100). The enzyme (e.g., alkaline phosphatase, luciferase) may be coupled to a binding partner (e.g., a protein such as an antibody or a receptor, for example). Sample materials can also be transferred into the reservoir 130 through the opening 120.

Sample materials include sample materials that are suspected of containing an analyte. The sample material may be a liquid, a solid, a solid suspended or dispersed in a liquid, a hydrogel. In any of the embodiments, the sample may comprise microorganisms and/or molecules that have been subjected to one or more sample preparation techniques including but not limited to concentration (e.g., by filtration, precipitation, agglomeration, centrifugation, absorption, and/or adsorption), amplification (e.g., growth-based and/or enzymatic amplification), enrichment (e.g., selective growth enrichment), extraction (e.g., cell lysis), and purification (e.g., chromatographic purification, solvent partitioning).

Providing a catalyst for a luminescent reaction comprises providing a substance that enables a luminescent reaction to proceed at a faster rate or under different conditions (e.g., at a lower temperature) than otherwise possible. In some embodiments, the catalyst is an enzyme such as luciferase (e.g., firefly luciferase) or alkaline phosphatase, for example. In some embodiments, the sample may comprise the catalyst. In some embodiments, the catalyst can be provided in a dry, rehydratable form. In some embodiments, the dry, rehydratable catalyst can be provided in the interior reservoir 115 of the container 110. In some embodiments, the catalyst may be provided in a separate container (not shown) and transferred to the interior reservoir 115. The catalyst may be rehydrated and/or diluted with an aqueous liquid (e.g., water, a buffer).

The method further comprises forming a reaction mixture in the container. The reaction mixture, when formed, comprises the catalyst for a luminescent reaction (e.g., luciferase) and the sample. The sample, either directly or indirectly, provides at least one reactant for the luminescent reaction. For example, in some embodiments, the sample may comprise cells or a cell lysate that provides ATP as a reactant for a bioluminescent reaction. Thus, in some embodiments, forming a reaction mixture further comprises forming a reaction mixture comprising a cell lysis agent (e.g., a detergent). In some embodiments, the sample may comprise nucleic acid (DNA or RNA) which, in the presence of the deoxyribonucleotide triphosphates and nucleic acid polymerase, can facilitate a polymerization reaction to form DNA or RNA. The polymerization reaction also results in the production of pyrophosphate ($P_2O_7^{4-}$) which, in the presence of adenosine monophosphate and ATP sulfurylase, can produce ATP, which can be used as a reactant for a bioluminescent reaction as described in Gandelman et al. Thus, in some embodiments, forming a reaction mixture further comprises forming a reaction mixture comprising to facilitate nucleic acid amplification. In some embodiments, forming a reaction mixture comprises forming a reaction mixture that includes nucleic acid precursors (e.g., dNTP's), a nucleic acid polymerase, and an enzyme (e.g., ATP sulfurylase) that uses pyrophosphate to produce a reactant (e.g., ATP) for a luminescent reaction.

Typically, forming a reaction mixture comprises placing the reactants in fluidic contact (e.g., in an aqueous fluid, such as an aqueous buffer, for example). The reaction mixture can be formed in the container 110, for example, by adding the reagents to the container either before or after adding an aqueous fluid to the container 110. Alternatively, the reaction mixture can be formed in a separate container (not shown) and a portion or all of the reaction mixture can be transferred to the container 110.

The method further comprises detecting the presence or absence of light emitted from the container or from contents therein. In some embodiments, detecting the presence or absence of light emitted from the container or light emitted from contents therein further comprises detecting light using a luminometer that includes a detector to detect light. In these embodiments, the method further comprises operably positioning the container in the luminometer such that light emitted from the container or light emitted from contents therein can be detected by the detector. In some embodiments, operably positioning the container in the luminometer further comprises positioning the container such that at least a part of the portion 115b of the wall comprising a coloring agent is positioned between the reaction mixture and the detector.

FIGS. 2A and 2B show one embodiment of a system 200 for detecting an analyte. FIG. 2A shows a partially-exploded longitudinal cross-sectional schematic view of the system 200 components. The system 200 includes a container 210 and a reader 240 that is similar to the diode-based device described by Gandelman et al. The container 210 comprises a wall 215 and a cap 218. The wall 215 includes a portion (e.g., the entire wall) that comprises a coloring agent. Disposed in the container 210 is a reaction mixture 230.

The reader 240 comprises a receiver 242 that includes a cavity 243 configured to receive the container. The receiver 242 can be fabricated from a variety of materials including, for example plastic or metal. In a preferred embodiment, the receiver 242 is fabricated from a heat-conducting material (e.g., aluminum), which is operationally coupled to a heat source (e.g., a resistor, not shown) and a temperature controller (not shown). In the illustrated embodiment, the cavity is shaped and dimensioned such that the container 215, excluding the cap 218, can be operationally coupled (i.e., fully and securely seated in) to the cavity 243 of the receiver 242.

Optionally, the reader 240 can comprise a light-collecting element 244. The light-collecting element 244 has a frustro-conical shape and is intended to collect light that is emitted from the container in a direction that is not toward the detector 248 and refract and/or reflect the light in a direction (arrow "A") that is toward the detector 248. In some embodiments, the light-collecting element 244 can be a mirror-like surface (e.g., a shaped, coated, and/or polished surface of the material used to fabricate the receiver 242).

The detector 248 can be any detector capable of converting photon signals (i.e., light) to electrical signals. Examples of suitable detectors 248 include, for example, photomultiplier tubes and photodiodes (e.g., avalanche photodiodes). The reader 240 further comprises a housing 260 and, optionally, a cover (not shown) to substantially exclude external light from the detector 248 when a sample is being analyzed by the reader 240.

FIG. 2B shows a cross-sectional longitudinal cross-sectional schematic view of the system 200 of FIG. 2A with the container 210 operably positioned in the reader 240. In the illustrated embodiment, because the entire wall comprises a coloring agent, operably positioning the container 210 further comprises positioning the container 210 such that at least a part of the colored portion of the wall 215 is positioned between the reaction mixture 230 and the detector 248.

In some embodiments, the reader 240 may be included in a luminometer. The luminometer can be a hand-held luminometer such as, for example, a LIGHTNING MVP System luminometer available from BioControl Systems, Inc., Bellevue, Wash. Alternatively, the luminometer can be a benchtop luminometer such as, for example, the 20/20$^n$ Single Tube Luminometer or a luminometer similar to those described in Gandelman et al.

According to the present disclosure, detecting the presence or absence of light emitted from the container is performed after forming the reaction mixture. The reaction mixture is configured such that the analyte in the sample provides a component that, either directly or indirectly, enables the luminescent reaction. Thus, the presence of light emitted from the container, or from contents (e.g., the reaction mixture) therein, after the reaction mixture is formed is an indication of the presence of the analyte in the portion of the sample that is tested. Conversely, the absence of light emitted from the container, or from contents therein, after the reaction mixture is formed is an indication of the absence of the analyte in the portion of the sample that is tested.

In some embodiments, detecting the presence or absence of light emitted from the container, or from contents therein, further comprises quantifying an amount of light emitted from the container. As used herein, detecting and/or quantifying light emitted from the container means detecting and/or quantifying at least some light that is emitted by contents of the container (e.g., a reaction mixture) and that passes through a colored portion of the container. In some embodiments, most of the detected and/or quantified light has been emitted by the contents of the container and has passed through a colored portion of the container.

In any of the embodiments of the method, the method further can comprise providing an analyte-specific reagent. In any of the embodiments, the analyte-specific reagent can comprise an analyte-specific polynucleotide (e.g., a primer that can be used to facilitate nucleic acid amplification). In any of the embodiments, the analyte-specific reagent can be provided (e.g., in a liquid medium or as a dehydrated reagent) in the container. In any of the embodiments, the color of the colored-portion of the container can be associated with the identity of the analyte-specific reagent provided in the container. Any color may be used to designate a container having an analyte-specific reagent. For example, a blue container may include an analyte-specific reagent to detect *Escherichia coli*, a yellow tube may include an analyte-specific reagent to detect *Staphylococcus aureus*, and/or a green tube may include an analyte-specific reagent to detect *Campylobacter jejuni*.

In another aspect, the present disclosure provides a kit to detect an analyte. The kit can comprise a container as described herein. The container comprises at least one wall that forms an opening and an interior reservoir. At least a portion of the wall comprises a coloring agent, as described herein. In some embodiments, the portion is visibly colored. The container further is adapted for use in a luminometer. The kit further comprises a catalyst for a luminescent reaction, as described herein. In any embodiment, the catalyst can comprise luciferase, for example.

In any embodiment, the kit further can comprise an analyte-specific reagent. In any embodiment, the analyte specific reagent can comprise a polynucleotide or an antibody, for example.

In any embodiment, the kit further can comprise a reagent used to extract and/or purify nucleic acid from a cell. Non-limiting examples of such reagents include a cell lysis reagent (e.g., a detergent, an enzyme, lysostaphin). In any embodiment, the kit further can include a reagent used to facilitate the amplification of nucleic acid (e.g., RNA polymerase, DNA polymerase, a mixture of ribonucleotide triphosphates, a mixture of deoxyribonucleotide triphosphates). In any embodiment, the kit further can include a reagent to facilitate the synthesis of ATP (e.g., ATP sulfurylase, adenosine monophosphate).

EMBODIMENTS

Embodiment A is a method of detecting an analyte, comprising:
 providing a sample; a catalyst for a luminescent reaction; a container that includes at least one wall;
 wherein the container is adapted for use in a luminometer;

wherein at least a portion of the wall comprises a coloring agent;

forming a reaction mixture in the container, the reaction mixture comprising the sample and the catalyst; and detecting the presence or absence of light emitted from the reaction mixture in the container.

Embodiment B is the method of embodiment A, wherein the container is adapted for use in a luminometer comprising a detector.

Embodiment C is the method of embodiment A or embodiment B, wherein forming a reaction mixture further comprises forming a reaction mixture to facilitate a luminescent reaction.

Embodiment D is the method of any one of the preceding embodiments, wherein the portion is visibly-colored.

Embodiment E is the method of any one of embodiments B through D, wherein detecting light from the container further comprises operably positioning the container in the luminometer.

Embodiment F is the method of embodiment E, wherein operably positioning the container further comprises positioning the container such that at least a part of the portion is positioned between the reaction mixture and a detector.

Embodiment G is the method of any one of the preceding embodiments, wherein detecting light further comprises quantifying an amount of light.

Embodiment H is the method of any one of the preceding embodiments, wherein providing the catalyst further comprises providing a dry, rehydratable catalyst.

Embodiment I is the method of any one of the preceding embodiments, wherein providing the catalyst comprises providing luciferase.

Embodiment J is the method of any one of the preceding embodiments, wherein providing the detection reagent and the container further comprises providing the container with the catalyst disposed therein.

Embodiment K is the method of any one of the preceding embodiments, further comprising providing an analyte-specific reagent.

Embodiment L is the method of embodiment K, wherein the color of the portion is associated with the identity of the analyte-specific reagent disposed in the container.

Embodiment M is the method of embodiment K or embodiment L, wherein providing an analyte-specific reagent further comprises providing an analyte-specific polynucleotide.

Embodiment N is the method of any one of the preceding embodiments, wherein forming a reaction mixture further comprises forming a reaction mixture to facilitate nucleic acid amplification.

Embodiment O is the method of any one of the preceding embodiments, wherein the analyte-specific reagent comprises DNA, RNA, or an enzyme-labeled protein.

Embodiment P is the method of any one of the preceding embodiments, wherein the color agent comprises a red coloring agent, a yellow coloring agent, a blue coloring agent, a green coloring agent, a mixture of any two or more of the foregoing coloring agents, or a combination of any two or more of the foregoing coloring agents.

Embodiment Q is a kit, comprising:
a catalyst for a luminescent reaction; and
a container comprising at least one wall;
wherein at least a portion of the wall comprises a coloring agent;
wherein the container is adapted for use in a luminometer.

Embodiment R is the kit of embodiment Q, wherein the portion is visibly-colored.

Embodiment S is the kit of embodiment Q or embodiment R, further comprising an analyte-specific reagent.

Embodiment T is the kit of embodiment S, wherein the reagent is disposed in the container.

Embodiment U is the kit of embodiment S or embodiment T, wherein the analyte-specific reagent comprises an analyte-specific polynucleotide.

Embodiment V is the kit of any one of embodiments S through U, wherein the color of the portion is associated with the identity of the analyte-specific reagent.

Embodiment W is the kit of any one of embodiments S through V, wherein the catalyst comprises luciferase.

Embodiment X is the kit of any one of embodiments S through W, further comprising a cell lysis agent, RNA polymerase, DNA polymerase, or ATP sulfurylase.

The present invention is illustrated by the following examples. It is to be understood that the particular examples, materials, amounts, and procedures are to be interpreted broadly in accordance with the scope and spirit of the invention as set forth herein.

EXAMPLES

Materials

Microbial Luminescence System LL1 Reagent and Microbial Luminescence System LL1 Buffer (both obtained from MLS L/L1 Replacement Kit, Catalog #3003B, available from 3M Health Care, St. Paul, Minn.)
Microbial Luminescence System (ATP) Positive Control (Catalog #3004; 3M Health Care; St. Paul, Minn.)
Molecular Grade Water; Catalog No. W4502; Sigma Chemical Co., St. Louis, Mo. 0.2 mL PCR tubes (#34267.8S clear, #34267.8B blue, #34267.8G green, #34267.8Y yellow, #34267.8L lavender, modified blue*, modified lavender*); Biotix; San Diego, Calif. The part numbers refer to the stock PCR tubes from Biotix. However, it should be noted that the modified blue and the modified lavender tubes used in the Examples were special-ordered and were made by Biotix using one-half of the amount (relative to the stock tubes) of coloring agent that is normally used to make the stock PCR tubes.
Hygiena Snapshot 1515 Universal ATP Surface Test; Hygiena, Camarillo, Calif.
BioControl Lightning MVP luminometer; BioControl Systems, Bellevue, Wash.

Comparative Example 1. Detection of Bioluminescence Using a Clear Microtube

Reagents:
Microbial Luminescence System LL1 reagent was reconstituted using the LL1 buffer and swirled to mix according to the manufacturer's instructions. 1 mL of the molecular-grade water was used to reconstitute the ATP Positive Control vial.

Construction of the hybrid devices: A 1-cm piece was cut off the bottom of SnapShot device tubes using a razor blade. Care was taken to ensure that the cut was approximately perpendicular to the longitudinal axis of the tube. The cap (with the attached swab) was removed from the device and about 5 cm of the swab shaft (including the fibrous bud) was broken off. The (cut) tube was shaken to expel any moisture that was loosely adhered to the walls of the tube. Clear 0.2 mL PCR tubes were cut from an 8-tube strip and the open end of the PCR tube was inserted into the cut openings in the bottom of the SnapShot tubes. The PCR tubes were inserted far enough into the SnapShot tubes so that about 1 cm of the PCR tubes extended out the bottom of the SnapShot tubes. The outer diameter of the PCR tube and the inner diameter of the SnapShot tube were of such similar dimensions that the PCR tube was firmly held in place, forming a liquid-resistant seal in the hybrid devices.

The blank samples were analyzed by pipetting 100 µL of the LL1 reagent into the clear PCR tube at the bottom of the hybrid devices, inserting the hybrid devices into a BioControl Lightning MVP luminometer, and obtaining an RLU reading according to the manufacturer's instructions. The test samples were analyzed by pipetting 10 µL of the ATP solution into the hybrid device, followed by 100 µL of the LL1 reagent. The solutions were mixed using a micropipet and the hybrid devices were inserted into a BioControl Lightning MVP luminometer to obtain an RLU reading according to the manufacturer's instructions. Five replicate devices were tested with each of the blank and the test solutions. It was noted that all of the liquid for each reaction (i.e., blank reactions and test reactions) was held in the PCR tube portion of the hybrid device while the hybrid device was placed in the luminometer to detect light emitted from the tube. The results are shown in Table 1. As an additional control, the empty hybrid devices (no LL1 Reagent and no ATP solution) were placed into the luminometer and the RLU reading was obtained.

Examples 1-4. Detection of Bioluminescence Using a Colored Microtube

Reagents and hybrid devices were prepared as described in Comparative Example 1 except that the blue PCR tubes were used to construct the hybrid devices for Example 1, the green PCR tubes were used to construct the hybrid devices for Example 2, the yellow PCR tubes were used to construct the hybrid devices for Example 3, and the lavender PCR tubes were used to construct the hybrid devices for Example 4. The "blank" (no ATP) and "test" RLU readings were obtained using the same methods described Comparative Example 1. The results are summarized in Table 1.

TABLE 1

Detection of a bioluminescent reaction using clear and colored reaction tubes. All results are reported as Relative Light units (RLU's).

|  | Blank | Test |
|---|---|---|
| Comparative Example 1 | 236 | 198450 |
| Comparative Example 1 | 201 | 205621 |
| Comparative Example 1 | 218 | 203080 |
| Comparative Example 1 | 241 | 187486 |
| Comparative Example 1 | 244 | 203546 |
| Ave. (Comp. Ex. 1) | 228 | 199637 |
| Example 1 | 263 | 175896 |
| Example 1 | 250 | 178749 |
| Example 1 | 221 | 174281 |
| Example 1 | 227 | 187653 |
| Example 1 | 228 | 190133 |
| Ave. (Ex. 1) | 238 | 181342 |
| Example 2 | 213 | 203855 |
| Example 2 | 240 | 191118 |
| Example 2 | 210 | 201122 |
| Example 2 | 233 | 193094 |
| Example 2 | 226 | 199193 |
| Ave. (Ex. 2) | 224 | 197676 |
| Example 3 | 266 | 199907 |
| Example 3 | 232 | 196112 |
| Example 3 | 225 | 188401 |
| Example 3 | 190 | 210654 |
| Example 3 | 209 | 202712 |
| Ave. (Ex. 3) | 224 | 199557 |
| Example 4 | 204 | 178512 |
| Example 4 | 217 | 177304 |
| Example 4 | 235 | 184201 |
| Example 4 | 223 | 174188 |
| Example 4 | 194 | 182196 |
| Ave. (Ex. 4) | 215 | 179280 |

The results show that the amount of light detected using the colored tubes ranged from about 89.9% (lavender tubes) to about 99.9% (yellow tubes) of the light detected using the clear tubes, even though the color of the tubes easily could be observed and identified by the human operator.

Example 5. Light Transmittance by Colored Microtubes

Figure 3:
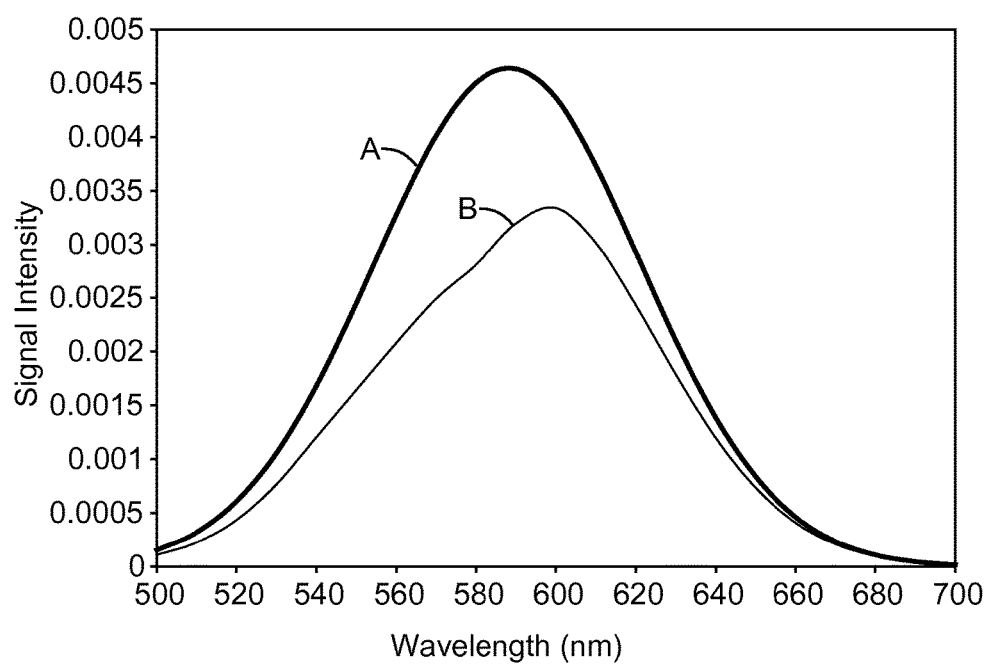
FIG. 3 is a graph of a portion of the spectrum of light emitted from luminescent reactions conducted in a clear container and a container comprising a coloring agent.

The transmittance of visible light by clear and colored PCR tubes was measured using a spectrophotometer (model number 80-2097-62, LKB Biochrom, Cambridge, UK). Reference scans were made with an empty cuvette. Experimental scans were made using individual cuvettes that contained the respective clear and colored Biotex PCR tube discussed above. FIG. 3 shows a comparison of the transmittance of 500-700 nm light through a clear PCR tube (line "A") and a modified lavender PCR tube (line "B"). Table 2 shows the results of an experiment where the transmittance of 500 nm-700 nm light through each of the various-colored PCR tubes was compared to the transmittance of light through a clear PCR tube. The experiment was performed as described above except that the reference scan was made using a cuvette containing a clear PCR microtube. Although all tubes transmitted at least 80% of the light transmitted by the clear tubes, the green, yellow, modified blue, and modified lavender tubes transmitted at least 90% of the light transmitted by the clear tubes.

TABLE 2

Detection of a light transmission through colored reaction tubes. All results are reported as Relative Light units (RLU's). Light transmittance was measured in tubes from three different lots of each stock PCR colored tube. Light transmittance was also measured in tubes from one lot each of the modified blue and modified lavender tubes.

|  | % | Ave. |
|---|---|---|
| Green Tube (lot A) | 89 | 92 |
| Green Tube (lot B) | 97 |  |
| Green Tube (lot C) | 91 |  |
| Blue Tube (lot A) | 83 | 89 |
| Blue Tube (lot B) | 94 |  |
| Blue Tube (lot C) | 92 |  |
| Yellow Tube (lot A) | 97 | 98 |
| Yellow Tube (lot B) | 99 |  |
| Yellow Tube (lot C) | 98 |  |
| Lavender Tube (lot A) | 83 | 84 |
| Lavender Tube (lot B) | 91 |  |
| Lavender Tube (lot C) | 80 |  |
| Modified Blue Tube | 98 |  |
| Modified Lavender Tube | 99 |  |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A kit, comprising:
a catalyst;
an analyte-specific reagent; and
a container comprising at least one wall,
wherein a material from which at least a portion of the wall is formed incorporates a coloring agent for marking the container;
wherein the container is adapted for use in a luminometer, and
wherein the portion of the wall comprising the coloring agent has an optical clarity and optical transmissivity that does not substantially prevent from passing through the portion of the wall of the container visible wavelengths of light that are products of a luminescent reaction in a reaction mixture comprising the catalyst and the analyte-specific reagent when the container contains the reaction mixture.

2. The kit of claim 1, wherein the portion of the wall is visibly-colored.

3. The kit of claim 1, wherein the analyte-specific reagent is disposed in the container.

4. The kit of claim 1, wherein the analyte-specific reagent comprises an analyte-specific polynucleotide.

5. The kit of claim 1, wherein the color of the portion of the wall is associated with the identity of the analyte-specific reagent.

6. The kit of claim 1, wherein the catalyst comprises luciferase.

7. The kit of claim 1, further comprising a cell lysis agent, RNA polymerase, DNA polymerase, or ATP sulfurylase.

8. The kit of claim 1, wherein the portion of the wall comprises at least about 40 percent of the wall.

9. The kit of claim 8, wherein the portion of the wall comprises at least about 70 percent of the wall.

10. The kit of claim 1, wherein, relative to a similar container that does not comprise the coloring agent, the container comprising the portion of the wall having the coloring agent permits the transmission of at least about 50% or more of the light emitted from the luminescent reaction.

11. The kit of claim 10 wherein, relative to a similar container that does not comprise the coloring agent, the container comprising the portion of the wall having the coloring agent permits the transmission of at least about 90% or more of the light emitted from the luminescent reaction.

* * * * *